United States Patent [19]
Chodorow

[11] Patent Number: 6,085,760
[45] Date of Patent: Jul. 11, 2000

[54] ANIMATE FORM DENTAL FLOSSING DEVICE

[75] Inventor: Ingram S. Chodorow, Upper Saddle River, N.J.

[73] Assignee: Placontrol, Inc., Rancho Santa Fe, Calif.

[21] Appl. No.: 09/001,897

[22] Filed: Dec. 31, 1997

[51] Int. Cl.[7] ................................. A61C 15/04
[52] U.S. Cl. ............................................... 132/323
[58] Field of Search .................... 132/323, 324, 132/329, 325, 326, 327; D28/65, 66, 67, 68

[56] References Cited

U.S. PATENT DOCUMENTS

| | | |
|---|---|---|
| D. 251,074 | 2/1979 | Schiff . |
| D. 256,955 | 9/1980 | Rogers ..................................... D28/64 |
| D. 301,071 | 5/1989 | Franchi . |
| 1,882,204 | 10/1932 | Zerna ...................................... 132/323 |
| 2,180,522 | 11/1939 | Henne ..................................... 132/323 |
| 2,443,415 | 6/1948 | Buscarino . |
| 2,702,555 | 2/1955 | De Mar ................................... 132/323 |
| 3,783,883 | 1/1974 | Alexander . |
| 3,926,201 | 12/1975 | Katz ........................................ 132/323 |
| 4,006,750 | 2/1977 | Chodorow .............................. 132/323 |
| 5,097,964 | 3/1992 | Fitz ........................................... 211/65 |
| 5,113,880 | 5/1992 | Honda et al. ........................... 132/321 |
| 5,246,021 | 9/1993 | Katz ........................................ 132/323 |
| 5,299,723 | 4/1994 | Hempel .................................... 225/38 |
| 5,692,531 | 12/1997 | Chodorow .............................. 132/323 |

*Primary Examiner*—Todd E. Manahan
*Assistant Examiner*—Eduardo C. Robert
*Attorney, Agent, or Firm*—Pitney Hardin Kipp & Szuch

[57] ABSTRACT

A dental flossing device replicating a dinosaur, includes a handle part extending in a first direction and a floss holder part extending from the handle part in a second direction different from the first direction. The handle and floss holder parts respectively are formed by shapes replicating (a) the head and open jaws and (b) the remaining body of a dinosaur, the jaws having proximal ends that are joined and distal ends that are spaced apart. The dental flossing device further includes a strand of dental floss extending generally linearly between and secured to the distal end of the jaws.

32 Claims, 4 Drawing Sheets

ANIMATE FORM DENTAL FLOSSING DEVICE

BACKGROUND OF THE INVENTION

1. Field of the Invention

This invention is in the field of dental flossing devices, of the type having a handle part and a flossing part, the latter holding a short strand of dental floss generally linearly.

2. Relevant Prior Art

The relevant prior art includes: dental floss devices that have a fixed shape such as Y or F or fork-shape with two tines; dental flossing devices which include means for varying the tension of the floss extending between the pair of arms or other floss-engaging means; and flossing devices which include means for replacing the strand of floss when it becomes frayed, thin, broken or otherwise deteriorated. Some flossers carry a spool of floss as the supply for substituting a new segment of floss to the device, while other merely have means to accommodate emplacement of a new segment of floss such as an aperture to receive and hold a knot at each end of the new segment of floss.

U.S. patents believed relevant to the present invention are listed below and deemed incorporated herein.

| D.244,376 | 5/1977  | Chodorow | D28/64  |
|-----------|---------|----------|---------|
| D.250,214 | 11/1978 | Chodorow | D28/64  |
| 4,006,750 | 2/1977  | Chodorow | 132/323 |
| 4,016,892 | 4/1977  | Chodorow | 132/91  |
| 5,086,792 | 2/1992  | Chodorow | 132/323 |

BACKGROUND

Dental flossing devices aid persons to floss their teeth by providing a device to hold a short strand of dental floss in generally linear fashion to be inserted between two adjacent teeth. This is in contrast to the traditional technique of taking a relatively long strand of floss about twelve to twenty inches, wrapping each end about a finger of each hand and manipulating the floss between the fingers into the interdental spaces.

All of the above-mentioned prior art dental flossing devices are intended to render flossing easier and more effective than the traditional technique of winding the ends of a long strand of floss about fingers of both hands and inserting fingers of one or both hands into the mouth to achieve flossing.

Flossing is generally not considered fun or easy. Thus, whether one uses the old technique or one of the relatively newer flossing devices, a strong motivation is often required. Many people and particularly children really do not want to floss for many reasons. Some do not believe or understand that it is important or effective; some think it takes too much time or it is difficult; some resist doing something which they may not do well; some object to putting their fingers in their mouths, or some simply do not want to do something that other persons are saying they should do. Also, many children lack the strength and dexterity in their fingers to properly use a long strand of dental floss or a prior art flosser.

OBJECTS OF THIS INVENTION

A first object of this invention is to provide a flossing device which will result in more frequent and/or more regular flossing, especially by children by inspiring or amusing or entertaining or cajoling them to use a flossing device. The flossing habit is best developed at a young age; it then becomes an automatic oral hygiene activity requiring no particular daily motivation.

A second object is to help children in particular to identify with a popular animated creature and thereby create or help encourage a positive and receptive state of mind as regards flossing teeth. Currently, dinosaurs are one of the popular creatures in children's storybooks and videos and in movies, the most famous being the BARNEY® dinosaur or those popularized in the two Jurassic Park movies. It is an object to provide a flosser that replicates a dinosaur with the dinosaur's open jaws holding the extended strand of dental floss. It is believed that such a creature-shaped flosser will enable children to relate better to the product.

An additional object is to provide a flossing device having a handle part which fits well in a young hand and thus is more easily and effectively used by children.

SUMMARY OF THE INVENTION

A dental flossing device replicating a dinosaur is formed of a handle part extending in a first direction and a floss holder device part extending from the handle part in a second direction different from the first direction, the floss holder and handle parts respectively formed by shapes replicating the head and open jaws, and the remaining body of a dinosaur. The jaws have proximal ends that are joined and distal ends that are spaced apart, with a strand of dental floss extending generally linearly between and secured to the distal ends of the jaws. The jaws have length in the direction from the proximal to the distal ends and cross-sectional area traversely of the length, the cross-sectional area being greater at the proximal ends than at the distal ends.

Preferred embodiments of the invention are disclosed below with reference to the drawings as follows:

DETAILED DESCRIPTION OF THE PREFERRED EMBODIMENTS

Figure 1:
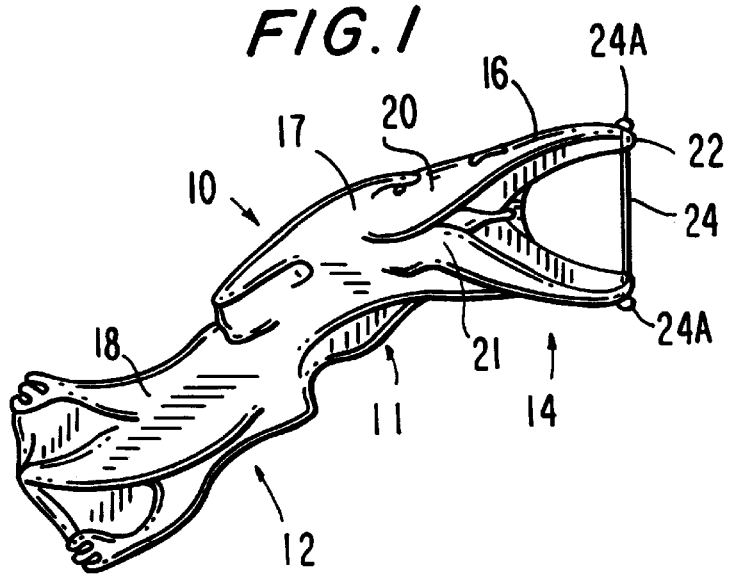
FIG. 1 is a front elevation view of a first embodiment of a Dinosaur Dental Flosser of my new invention.
Figure 2:
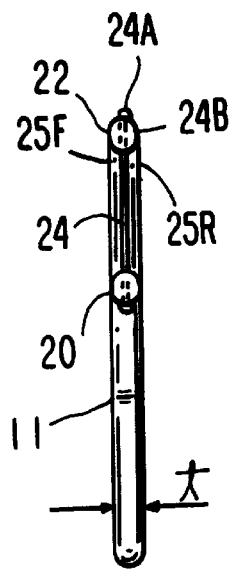
FIG. 2 is a right side elevation view thereof.
Figure 3:
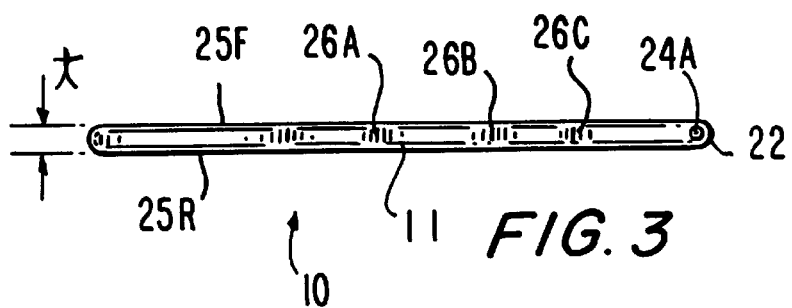
FIG. 3 is a bottom plan view thereof.

FIG. 1 shows a first preferred embodiment 10 of my new dinosaur dental flosser formed of a central part 11, a handle part 12 extending in a first direction from said central part and a floss holder part 14 extending in a second direction different from said first direction. The floss-holder part 14 is formed by open jaws 16 while the handle 12 is formed by one part 17 replicating a dinosaur's head and a stem part 18 replicating the remaining body of a dinosaur. The open jaws 16 have proximal ends 20 which are joined and remote ends 22, each jaw being generally tapered from its proximal to its remote end such that the proximal end has greater cross-sectional area than the distal end. As seen in FIGS. 2 and 3, the flosser is generally thin, flat elongate strip (having thickness t) despite its dinosaur appearance in the front elevation. A strand of multi-filament ultra high molecular weight polyethylene 24 extends between and is secured to said terminal ends 22 of the jaws 16.

This device may be simply defined as having a handle and extending therefrom a floss-holding part. The dental flossing handle 12 is made and the dental floss 24 is secured to the handle by a prior art method and apparatus disclosed in various of my cited prior art references cited herein and elsewhere, namely with the handle 12 being injection molded in a multi-cavity mold (not shown herein) and with the dental floss 24 positioned and molded "in situ" into the jaws. The plastic in this preferred embodiment is polypropylene; however many other plastics could be used including nylon, polystyrene, or polycarbonate.

As seen in FIGS. 1 and 2 the floss is further secured to or in the jaws by having its ends 24A, extending through and protruding outward of the jaws. By subsequent heating of the protruding floss, the ends of each of the filaments in the multifilament fiber floss are caused to coalesce into bead form. The resulting floss end has greater cross-sectional diameter than the diameter of the original strand of floss or the diameter of the aperture 24B in the jaw 22 through which the floss extends. Under normal and reasonable the larger diameter beaded end of the floss cannot be pulled through the terminal end of the jaw and thus is secured permanently hereto. The floss itself, when selected from lubricous high strength ultra high molecular weight polyethylene will not break under normal and reasonable use. A variety of other floss compositions may be used, such as multifilamented nylon, PTFE ribbon, etc., but floss should be selected by its characteristics most compatible with the injection molded plastic being used for the handle. In each of the embodiments shown the length of the strand of dental floss extending between the distal ends of the jaws is greater than the distance from the floss to the proximal ends of the jaws.

The shape and structure of the floss holder part 14, namely the open jaws 16 not only contributes to the dinosaur or animated theme which is a significant feature discussed below, but provides new structural strength at a critical jaw junction 21 area not addressed in the prior art.

The floss holder of FIG. 1 has similar front and rear surfaces 25F, 25R as seen in the right elevation and bottom plan views of FIGS. 2 and 3 respectively. Transverse lines 26a and 26b and 26c in FIG. 3 indicate corresponding hip and jaw portions in FIG. 1. Thus, the article of FIGS. 1–3 is similar on the front and rear and is a three-dimensional replica or copy of a dinosaur.

Figure 4:
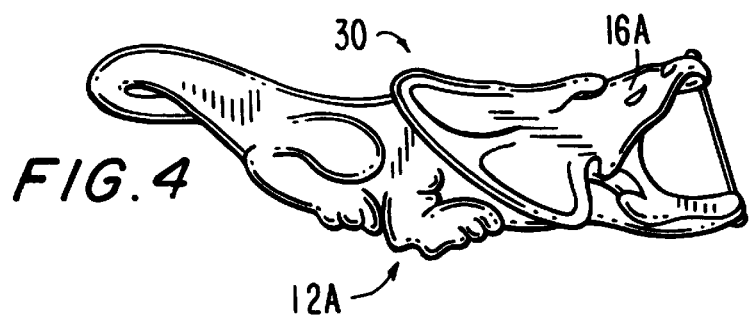
FIG. 4 is a front elevation view similar to FIG. 1 of a second embodiment of my invention.
Figure 5:
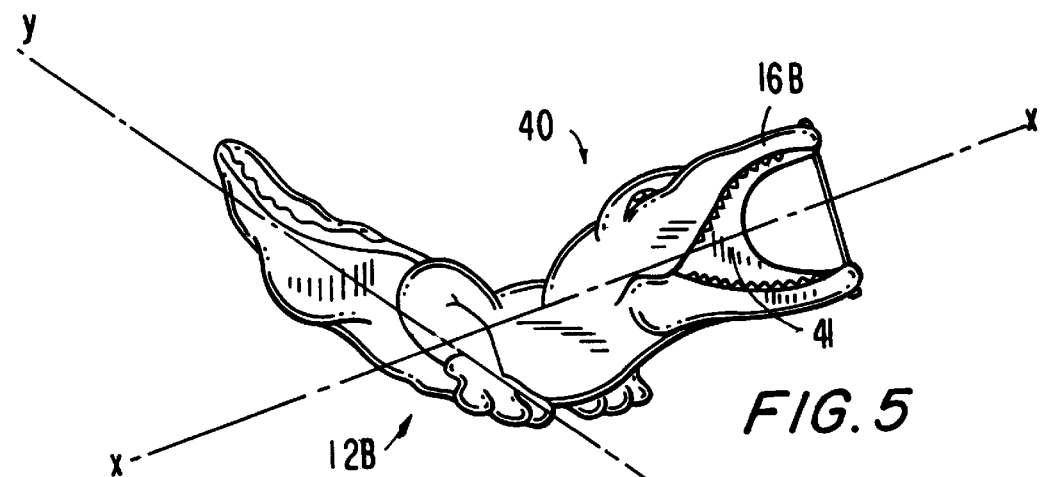
FIG. 5 is a front elevation view similar to FIG. 1 of a third embodiment of my invention.
Figure 6:
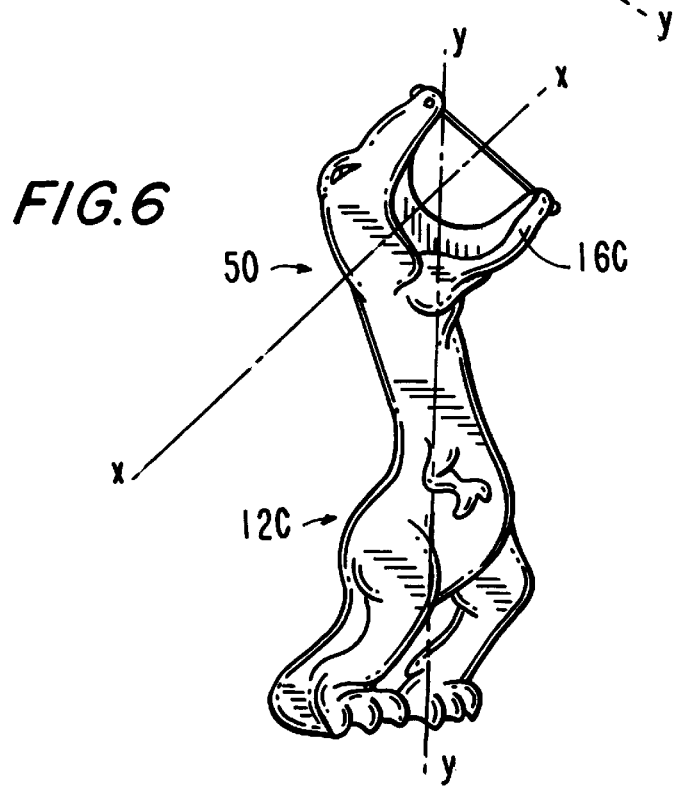
FIG. 6 is a front elevation view similar to FIG. 1 of a fourth embodiment of my invention.

FIGS. 4, 5 and 6 show three other embodiments 30, 40 and 50 of the new dinosaur flosser. Parts of these embodiments that correspond to basic parts of the FIG. 1 embodiment are provided with the same reference numbers followed by A, B or C respectively in FIGS. 4, 5 and 6. In FIG. 5, for example, the jaws 16B define between them a web 41 which greatly strengthens the floss-holding structure while not detracting from the dinosaur replication.

The dinosaurs of FIGS. 4, 5 and 6 demonstrate variations in angulation of the handle parts 12A, 12B and 12C relative to the jaws. In FIG. 4 the handle part is generally perpendicular to the strand of floss in the floss holder part. In FIG. 5, the jaws have a longitudinal axis x—x and the handle 12B has a longitudinal axis y—y at almost 45° from said x—x axis. In FIG. 6 the jaws axis x—x is about 45° from the handle axis. In FIG. 6 the abdomen or tummy part is bulbous to be easily gripped like a ball for some children. In FIGS. 4 and 5 the handles are substantially tapered to a minimum terminal end which will be preferable for gripping for other children.

Earlier F and Y style dental flossers primarily provided a pair of spaced apart arms to hold the strand of floss. The focus apparently was to leave substantial clearance space between the arms to have thin arms to minimize plastic, and to focus on materials suitable for high volume manufacture and secure engagement with the arms. Now that these objectives have been partially achieved in the prior art, the present invention has focused on how to motivate children to floss regularly and properly, and how to provide a dental floss holder that is compatible with the new high strength floss and the vigorous use and stress to which it is subjected.

The present invention solves both of these issues with a dinosaur shape or replication that is highly popular with children at present and a dinosaur open jaw shape which has greater cross-section at the base where the jaws are joined to provide maximum strength against the maximum bending moment exerted when the floss is tensioned and the jaws are stressed to bend during flossing activity.

This dinosaur or animated theme provides a further structural and functional benefit over prior art flossers, many of which have a relatively thin stem-like handle. Such handle shape was chosen as it seemed adequate, and the minimum size reduced plastic and cost. As the present invention is focused for use by children, it was discovered that children's hands and fingers being not so strong and dexterous as adults' could greatly benefit from a handle of maximum cross-sectional dimension as compared to prior art handles of minimum cross-section. This concept has been carried still further by having the handles of some embodiments shaped to conform generally to the surfaces of a child's closed hand. By using a dinosaur head and body for the handle shape, this invention is able to continue the theme of animation and simultaneously provide a substantially wide diameter handle which is used more easily and more effectively by children.

Within this animation theme it is intended to apply the new concept to creatures other than dinosaurs, such as animals, fish and humans. Thus, a new dental floss holder part may have the form of open jaws of various creatures or may use a pair of spaced apart arms or legs or other projections of the creature. These spaced floss-engaging elements may have a generally V-shape or U-shape or still other shape, so long as they are sufficiently long, sufficiently spaced apart and sufficiently strong both as regards bending strength and ability to engage and securely hold the floss.

Figure 7:
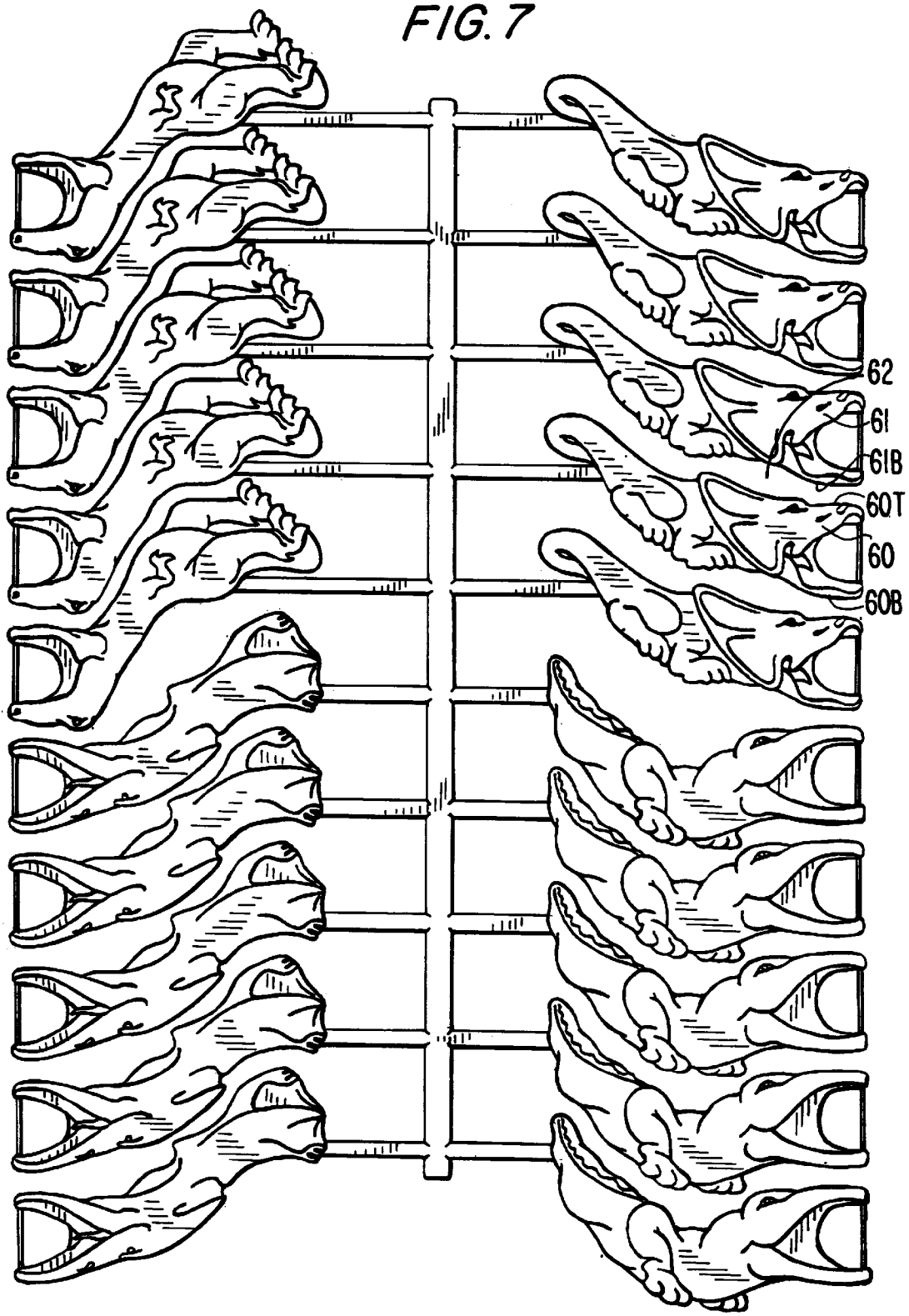
FIG. 7 is a schematic drawing of a multicavity mold showing aligned and adjacent cavities for similar dental flossing devices.
Figure 8:
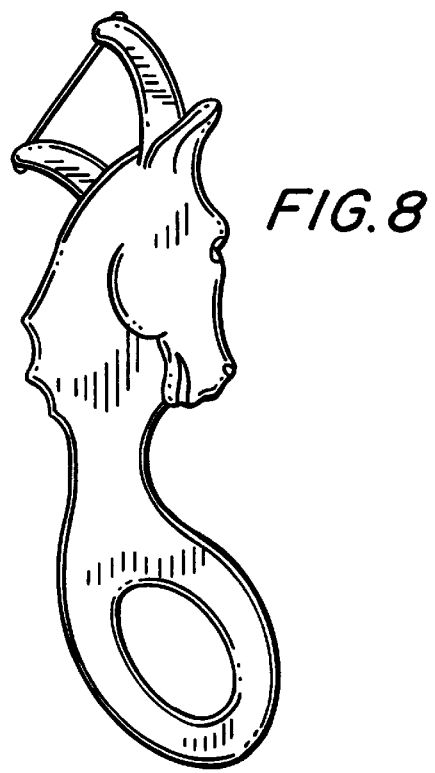
FIG. 8 is a front elevation view of a dental flosser with a pair of horns holding the floss.
Figure 9:
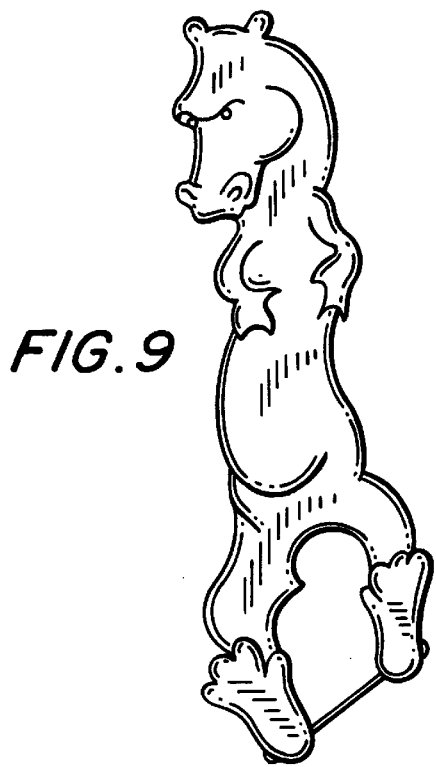
FIG. 9 is similar to FIG. 8 with a pair of legs holding the floss.
Figure 10:
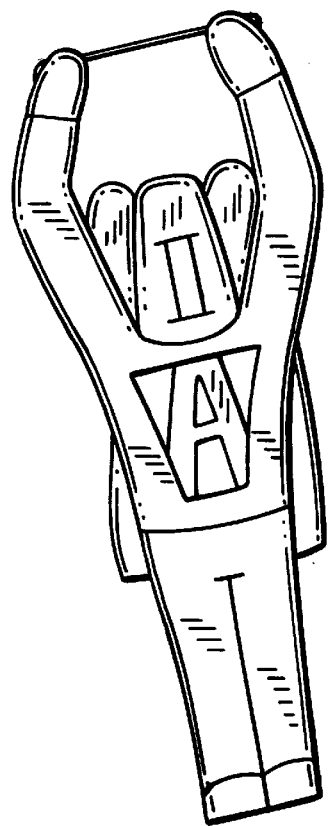
FIG. 10 is similar to FIG. 8 with a pair of arms holding the floss.

As indicated schematically in FIG. 7, in the manufacture of these animate form dental flossing devices it is contemplated that multi-cavity molds 25 be used with well-known injection molding techniques. With these animated shapes as exemplified in FIG. 7 the plurality of cavities 26a, 26b, 26c, 26d are adjacent, aligned and oriented to permit a maximum of cavities in the minimum amount of space while still having a single strand of floss 27 co-axial through a plurality of pairs of jaws 28a, 28b, 28c, 28d. This provides both high efficiency in molding costs and efficiency and great convenience in subsequent packaging, whereby a group of molded devices are automatically correctly positioned, spaced and oriented and maintained separate for automatic packaging operations.

The dinosaur or other animate shapes are conducive for use in this multiple aligned arrangement where the plurality of heads are mutually adjacent and their corresponding body parts are mutually adjacent. As seen in FIG. 7 each replicated dinosaur shape has a top jaw and top of the head and body and a bottom jaw and a bottom of the head and body. The top parts of one replicated dinosaur are closely adjacent the bottom parts of the next replicated dinosaurs. As noted above, this aids in efficiency and economy, and furthermore is esthetically pleasing for later packaging. FIG. 7 includes four groups or sets of different dinosaurs, I–IV, but any mold could have all the same shapes or various different ones.

Where the animate object replicates a dinosaur or other animal the replicated teeth in the jaws may actually protrude or preferably will be included in the mold design to appear but not actually protrude as seen in FIG. 5.

As discussed above, the handle portion of the new dental flosser devices may have the shape of a dinosaur head and body or other animate object. In these cases the handle has breadth B or cross section substantially as great as the breadth of the floss holder part or of the length L of the strand of floss as exemplified in FIG. 4. Thus, the handle part is easily grippable by a youngster.

The above described embodiments of this invention may take a variety of other forms still within the spirit of this invention and within the scope of the claims appended hereto.

What is claimed is:

1. A dental flossing device replicating a three-dimensional dinosaur having open jaws, a head, and body parts, said dental flossing device comprising an injection molded handle part extending in a first direction and a floss holder part extending from the handle part in a second direction different from the first direction, said floss holder and handle parts respectively formed by three-dimensional shapes replicating (a) said open jaws and (b) said head and body parts of a dinosaur, said jaws having proximal ends that are joined and distal ends that are spaced apart, said dental flossing device further comprising a strand of dental floss extending generally linearly between and permanently secured to said distal ends of said jaws by injection molded plastic of said handle molded about said strand, said handle part has a proximal end adjacent said floss holder part and an opposite distal end and length between said proximal and distal ends said handle part having a maximum breadth substantially similar to a maximum breadth of said holder part, so as to facilitate gripping by a person.

2. A dental flossing device according to claim 1 wherein said handle comprises five projections replicating four legs and a tail of said dinosaur.

3. A dental flossing device according to claim 2 wherein said handle part has a proximal portion adjacent to said dental floss part and an opposite distal portion, said distal portion of said handle part tapers to a smaller cross-section relative to said proximal portion thereof, said distal portion replicating said tail of said dinosaur.

4. A dental flossing device according to claim 3 wherein said handle part tapers to a terminal end remote from said floss-holding part.

5. A dental flossing device according to claim 1 wherein said handle comprise s at least two projections replicating legs of said dinosaur.

6. A dental flossing device according to claim 1 wherein each of said jaws further comprises a row of teeth, the teeth in each jaw pointing toward the teeth in the other jaw.

7. A dental flossing device according to claim 1 wherein said strand of floss has length dimension L between said jaws, and wherein said handle part has a proximal portion adjacent said floss holder part and an opposite distal portion and length therebetween comprising proximal and distal halves respectively of said handle part, said proximal half replicating the head and at least part of the body of said dinosaur, said proximal half having transverse cross-sectional dimension along its length at least as great as said dimension L.

8. A dental flossing device according to claim 1 wherein said dental floss comprises multifilament ultra-high molecular weight polyethylene.

9. A dental flossing device according to claim 8 wherein said handle and floss holder parts are contiguous injection molded plastic, and said strand of dental floss is molded in situ into said floss holder part.

10. A dental flossing device according to claim 8 wherein said strand of floss extends through each of said jaws and extends outward thereof as an exposed end, and each of said exposed ends comprises a plurality of filaments whose ends after being heated form a bundle of coalesced beads at the ends of the fibers.

11. A dental flossing device according to claim 1 wherein said handle and floss holder parts are contiguous injection molded plastic, and said strand of dental floss is molded in situ into said floss holder part.

12. A dental flossing device according to claim 1 wherein said open jaws are generally parallel.

13. A dental flossing device according to claim 1 wherein said open jaws define a generally elongated V shape.

14. A dental flossing device according to claim 1 wherein said first and second directions are generally opposite.

15. A dental flossing device according to claim 1 wherein said strand of dental floss extends generally linearly and generally perpendicular to said first direction.

16. A dental flossing device according to claim 1 wherein said handle has a longitudinal axis and said jaws have a longitudinal axis generally 45 degrees inclined with respect to the longitudinal axis of said handle.

17. A dental flossing device according to claim 1 wherein said handle has a longitudinal axis and said jaws have a longitudinal axis inclined with respect to the longitudinal axis of said handle.

18. A dental flossing device according to claim 1 wherein said handle has a longitudinal axis and said strand of dental floss has a longitudinal axis inclined with respect to the longitudinal axis of said handle.

19. A dental flossing device according to claim 1, wherein said strand of dental floss is situated a distance D from said proximal ends of said jaws, and said strand of dental floss extending between said distal ends of said jaws has length greater than said distance D.

20. A dental floss holder according to claim 1 wherein jaws have breadth D1 between them and said handle has breadth D2, where D2 is substantially as great as D1.

21. A dental flossing device replicating an three-dimensional animate object, said dental flossing device comprising an injection molded handle part extending in a first direction and a floss holder part extending from the handle part in a second direction different from the first direction, said floss holder and handle parts respectively formed by three-dimensional shapes replicating (a) two projections from said animate object and (b) a body of said animate object, said two projections having proximal ends that are joined and distal ends that are spaced apart, said dental flossing device further comprising a strand of dental floss extending generally linearly between and permanently secured in said distal ends of said projections by injection molded plastic of said handle molded about said strand, said handle part has a proximal end adjacent said floss holder part and an opposite distal end, and length between said proximal and distal ends said handle part having a maximum breadth substantially similar to a maximum breadth of said holder part, so as to facilitate gripping by a person.

22. A dental flossing device according to claim 21 wherein said two projections replicate a pair of arms or legs or horns of said animate objects.

23. A dental flossing device according to claim 21 wherein said two projections comprise a pair of open jaws of said animate object.

24. A dental flossing device according to claim 21 wherein said handle and floss holder parts are contiguous injection molded plastic, and said strand of dental floss is molded in situ into said floss holder part.

25. A dental flossing device according to claim 21 wherein said dental floss comprises multifilament ultra-high molecular weight polyethylene.

26. A dental flossing device according to claim 25 wherein said strand of floss comprises a plurality of filaments, and said strand of floss extends through each of said projections and extends outward thereof as an exposed end, and said plurality of filaments comprising each of said ends has been heated to form a bundle of coalesced beads at the ends of said filaments.

27. A plurality of the dental flossing devices each of which replicates a three-dimensional dinosaur having open jaws, a head, and body parts and comprises an injection molded handle part extending in a first direction and a floss holder part extending from the handle part in a second direction different from the first direction, said floss holder and handle parts respectively formed by three-dimensional shapes replicating (a) said open jaws and (b) said head and body parts of a dinosaur, said jaws having proximal ends that are joined and distal ends that are spaced apart, said dental flossing device further comprising a strand of dental floss extending generally linearly between and permanently secured to said distal ends of said jaws by injection molded plastic of said handle molded about said strand, said handle part has a proximal end adjacent said floss holder part and an opposite distal end and length between said proximal and distal ends, said plurality of dental flossing devices being aligned, spaced apart and oriented similarly and wherein said strands of floss of said devices comprises a single strand extending co-linearly through all said devices, said handle part having a maximum breadth substantially similar to a maximum breadth of said holder part, so as to facilitate gripping by a person.

28. A plurality of dental flossing devices according to claim 27, where each of said devices has a terminal end of its body and has curvature along its length from its jaws to said terminal end, and said devices are oriented so that the curvature of each matches the curvature of the adjacent device.

29. A plurality of dental flossing devices as defined in claim 27, where for each of said devices the replicated dinosaur comprises a top and a bottom, where the top includes one of said open jaws and the top of the head and body, and the bottom includes the other of said open jaws and the bottom of the head and body, said devices being oriented with the top of one adjacent the bottom of the adjacent one.

30. A plurality of dental flossing devices according to claim 29, where each of said devices is closely adjacent the next.

31. A plurality of dental flossing devices, each of which replicates a three-dimensional dinosaur having opening jaws, a head, and body parts and comprises an injection molded handle part extending in a first direction and a floss holder part extending from the handle part in a second direction different from the first direction, said floss holder and handle parts respectively formed by three-dimensional shapes replicating (a) said open jaws and (b) said head and body parts of a dinosaur, said jaws having proximal ends that are joined and distal ends that are spaced apart, said dental flossing device further comprising a strand of dental floss extending generally linearly between and permanently secured to said distal ends of said jaws by injection molded plastic of said handle molded about said strand, said handle part has a proximal end adjacent said floss holder part and an opposite distal end and length between said proximal and distal ends, and wherein each of said devices is identical in shape and each has opposite top and bottom edges which are different from each other, and where for each two adjacent devices the top edge of one is spaced apart from the bottom edge of the other, and said top and bottom edges have overall curvatures that generally correspond resulting in an elongate gap of generally constant width between them, said strand of dental floss being continuous and extending generally axially from said jaws of each of said devices to the jaws of the adjacent device, and said handle part having a maximum breadth substantially similar to a maximum breadth of said handle part, so as to facilitate gripping by a person.

32. A method of making a plurality of dental floss holder devices each of which devices replicates a three-dimensional dinosaur having a handle part extending in a first direction and a floss holder part extending from the handle part in a second direction different from the first direction, said floss holder and handle parts respectively formed by three-dimensional shapes replicating (a) open jaws and (b) a head and body of a dinosaur, said jaws having proximal ends that are joined and distal ends that are spaced apart, said dental flossing device further comprising a strand of dental floss extending generally linearly between and permanently secured to said distal ends of said jaws and said handle part having a maximum breadth substantially similar to a maximum breadth of said holder part, so as to facilitate gripping by a person, comprising the steps of:

a forming a multicavity mold with each cavity having a shape corresponding to one of said devices, said mold having plurality of said cavities oriented similarly with the heads of said dinosaurs being mutually parallel and with a single strand of floss extending through all their jaws, and with the head and body of each dinosaur being spaced apart from the corresponding head and body of the next adjacent dinosaur, b positioning a single strand of said floss to extend coaxially through all said pairs of jaws, and c injection molding fluid plastic into said cavities, with said dental floss molded in situ within said plastic which forms said jaws.

* * * * *